(12) United States Patent
Fiesser

(10) Patent No.: US 9,597,294 B2
(45) Date of Patent: Mar. 21, 2017

(54) CONTINUOUS COATING OF PELLETS

(71) Applicant: GlaxoSmithKline LLC, Wilmington, New Castle, DE (US)

(72) Inventor: Frederick Henry Fiesser, Collegeville, PA (US)

(73) Assignee: GlaxoSmithKline LLC, Wilmington, New Castle, DE (US)

( * ) Notice: Subject to any disclaimer, the term of this patent is extended or adjusted under 35 U.S.C. 154(b) by 37 days.

(21) Appl. No.: 14/514,464

(22) Filed: Oct. 15, 2014

(65) Prior Publication Data

US 2015/0030756 A1  Jan. 29, 2015

Related U.S. Application Data

(62) Division of application No. 12/527,885, filed as application No. PCT/US2008/054192 on Feb. 18, 2008, now Pat. No. 8,887,659.

(60) Provisional application No. 61/021,436, filed on Jan. 16, 2008, provisional application No. 60/890,892, filed on Feb. 21, 2007.

(51) Int. Cl.
| | |
|---|---|
| *A61K 9/50* | (2006.01) |
| *B05C 3/05* | (2006.01) |
| *B05C 19/02* | (2006.01) |
| *B05C 5/02* | (2006.01) |
| *B05C 9/08* | (2006.01) |
| *B05C 13/00* | (2006.01) |
| *B01J 2/00* | (2006.01) |
| *B05B 13/02* | (2006.01) |
| *B05D 1/02* | (2006.01) |
| *B01J 2/18* | (2006.01) |
| *A61J 3/00* | (2006.01) |
| *A01C 1/06* | (2006.01) |
| *A23G 3/26* | (2006.01) |
| *B05D 1/22* | (2006.01) |
| *B05D 3/12* | (2006.01) |

(52) U.S. Cl.
CPC ............. *A61K 9/5089* (2013.01); *B01J 2/006* (2013.01); *B05B 13/0257* (2013.01); *B05C 3/05* (2013.01); *B05C 5/022* (2013.01); *B05C 5/0216* (2013.01); *B05C 9/08* (2013.01); *B05C 13/00* (2013.01); *B05C 19/02* (2013.01); *B05D 1/02* (2013.01); *A01C 1/06* (2013.01); *A23G 3/26* (2013.01); *A61J 3/005* (2013.01); *B01J 2/18* (2013.01); *B05D 1/22* (2013.01); *B05D 3/12* (2013.01); *B05D 2258/00* (2013.01)

(58) Field of Classification Search
CPC .................................................. B05B 13/0257
See application file for complete search history.

(56) References Cited

U.S. PATENT DOCUMENTS

| | | | |
|---|---|---|---|
| 3,733,056 A * | 5/1973 | Fong | ................... B01F 13/0283 34/583 |
| 3,765,532 A | 10/1973 | Morris et al. | |
| 4,050,406 A | 9/1977 | Reni | |

(Continued)

OTHER PUBLICATIONS

EPO, Examination Report on European Application 08 730 071.1.

*Primary Examiner* — Robert Vetere
(74) *Attorney, Agent, or Firm* — Dara L. Dinner; Michael Lubienski; Richard Easeman

(57) ABSTRACT

A continuous dosage form coating apparatus uses vibrational impulses to maintain a dosage forms in a fluid state to expose them to a coating material atomized by spraying.

13 Claims, 6 Drawing Sheets

(56) References Cited

U.S. PATENT DOCUMENTS

| | | | |
|---|---|---|---|
| 4,066,024 A * | 1/1978 | O'Connor | B01J 8/10 |
| | | | 110/245 |
| 4,256,785 A | 3/1981 | Dannelly | |
| 4,576,572 A * | 3/1986 | Mueller | F27B 7/162 |
| | | | 432/105 |
| 5,067,431 A | 11/1991 | Heitmiller | |
| 5,140,756 A | 8/1992 | Iwaya et al. | |
| 5,567,238 A | 10/1996 | Long, Jr. et al. | |
| 5,615,606 A | 4/1997 | Vos | |
| 5,648,118 A * | 7/1997 | Liborius | B01J 2/16 |
| | | | 427/212 |
| 5,721,012 A | 2/1998 | Long, Jr. et al. | |
| 6,048,571 A | 4/2000 | Kohno et al. | |
| 6,274,190 B1 * | 8/2001 | Long, Jr. | A01C 1/06 |
| | | | 427/2.15 |
| 7,008,668 B2 | 3/2006 | Hogan et al. | |
| 2001/0016224 A1 | 8/2001 | Huttlin | |
| 2002/0113925 A1 * | 8/2002 | Higashi | G02B 5/08 |
| | | | 349/113 |
| 2003/0031786 A1 * | 2/2003 | Rumpler | A23L 1/002 |
| | | | 427/212 |
| 2003/0044524 A1 * | 3/2003 | Hoffland | B05C 19/025 |
| | | | 427/180 |
| 2003/0200920 A1 | 10/2003 | Jones et al. | |
| 2004/0089230 A1 | 5/2004 | Schwarz et al. | |
| 2005/0152217 A1 | 7/2005 | O'Hara | |
| 2005/0199859 A1 | 9/2005 | Terada et al. | |
| 2006/0017916 A1 * | 1/2006 | Clarke | A61J 3/00 |
| | | | 356/300 |

\* cited by examiner

CONTINUOUS COATING OF PELLETS

FIELD OF THE INVENTION

This invention relates to systems, methods and apparatuses for applying coatings to pellets, and has particular utility in coating pharmaceutical dosage forms and other pellet-shaped materials.

BACKGROUND OF THE INVENTION

Dosage forms, such as compressed tablets, chewable tablets, fast dissolving tablets, capsules, softgels, and gelcaps are known in the pharmaceutical arts. Production of these dosage forms is often carried out in steps. Some production steps are continuous, and others are carried out as "batch" processes. The distinction is that, in a continuous production step, the dosage forms can be fed to and withdrawn from a processing stage continuously, usually without any time limit, whereas in batch processing, a quantity of dosage forms is fed to a processing stage, and then processed and withdrawn.

In the manufacture of many of these dosage forms, it is common to coat pellets with films or with layers of films. In the case of pharmaceutical products, the coatings can have a number of purposes. The coatings can be cosmetic, pharmaceutically active, or otherwise functional. For example, a coating can be used to prevent a portion of a drug from being released in the form of dust. It can be used to mask an unpleasant odor or taste of the active drug, or of a filler or binder. It can be used to facilitate swallowing by providing the dosage form with a smoother and less absorbent outer layer. A coating resistant to gastric fluids can be used to prevent premature digestion of the contents of a dosage form. A coating can also control the rate of absorption of the drug by the small intestine. A coating can also be used to provide a dose of another drug in combination with the base dosage form. Finally, a coating can improve the appearance of the tablet, impart a distinctive color to the tablet for identification, and provide a printable surface.

Dosage forms are often coated using machines which spray a liquefied coating material onto the surfaces of the dosage forms while the dosage forms are in motion within a container. Examples of typical liquefied coating materials, include hydroxypropylmethylcellulose (HPMC) and starch-based materials. These coating materials may or may not include pigment, Two common types of machines tumble tablets within a drum that rotates about a horizontal axis during the spraying process.

The coating step for pharmaceutical volume products is most often a batch process, and in the most commonly used batch process, a perforated pan coating machine is used. The perforated pan machine includes a rotating, perforated drum which rotates about a horizontal axis within a housing, and further includes a plurality of nozzles positioned within the drum. The nozzles create a spray of coating material within the drum so that dosage forms located within the drum will tumble about into and out of the spray pattern and, over a period of time, accumulate a coating on their surfaces.

Appropriate ducting is used to direct air through the housing of the perforated pan machine so that it passes through the perorated drum and reaches the dosage forms tumbling therein. The perforations of the drum expose the tumbling dosage forms to a current of air, resulting in more uniform drying. The drum further includes baffles, which enhance mixing of the dosage forms in order to improve the distribution of the material being sprayed onto the tablets.

Unfortunately, batch coating has drawbacks. For example, each of the various apparatuses employed in batch coating is housed in a separate clean room that must meet standards set by the Food and Drug Administration. This requires a relatively large amount of capital in terms of space and machinery.

Batch coating processes are also difficult to control because the control algorithms attempt to control the process toward a difficult-to-define endpoint, rather than control a continuous process where parameters can be controlled using feedback.

Heretofore, batch coating processes have inhibited manufacturers from interconnecting process stages, and from flexibly interconnecting continuous stages of various kinds and capabilities to meet manufacturing requirements. A process that would increase and streamline production rates by coupling continuous processing stages in line would provide many economic benefits, including a reduction in the size of facilities needed for mass production of pharmaceutical products. Generally, it would be desirable to create a continuous coating process for the formation of tablets and other dosage forms, so that linkages can be made with other similar or different operations such as tablet compression. By making such linkages, it will be possible to carry out dosage form production in an overall continuous process.

Continuous coating processes for dosage forms also exist. An example is the model CC-3015 continuous coater made by O'Hara Technologies of Richmond Hill, Ontario, Canada. These continuous coating processes utilize rotating cylinders, and are generally limited to relatively large throughput volumes. The reason is that there are practical limits on how close the spraying systems can be to the bed of pellets to be coated. The required spray-to-bed distance, and also the need to accommodate monitoring sensors in the vicinity of the product being coated, imposes a limit on how small the diameter of the cylinder can be, and therefore limits the ability of a manufacturer to scale down a continuous coating process to lower throughput volumes. Thus, while continuous coating is useful in the production of non-prescription products such as calcium supplements, antacids, and other products sold in high volumes, it is difficult to scale down a continuous coating machine to make it practical for use with lower throughput volumes such as in the case of most prescription drugs. Consequently, coating of many prescription drugs is still carried out in a batch mode.

Another problem common to the existing batch coating machines and continuous coating machines is that shear forces and stresses encountered by tablets in these machines can cause splitting or chipping of tablets, especially multi-layer tablets and tablets having less physically robust formulations.

SUMMARY OF THE INVENTION

The invention provides for continuous exposure of pellets, e.g., dosage forms such as medicinal tablets, to the spray of a coating apparatus without the use of a rotating cylinder, and therefore without any minimum cylinder size limitation. Process monitoring and feedback is also made easier because of the elimination of the constraints imposed by the rotating cylinder.

Briefly, in the case of a rotating cylinder, the spraying apparatus must be inside the cylinder, and may therefore be too close to the bed of pellets in the case of a cylinder having a relatively small-diameter. The invention avoids the limitation on the height of the spraying apparatus by utilizing vibration to induce rolling motion of a bed of pellets in a trough. The trough can be open at its top, or, if enclosed, can be of a shape such that the spray nozzles can be disposed at the required distance from the pellet bed. The trough can have, but does not necessarily have, an arc-shaped transverse cross-section.

Vibratory finishing has been used for a long time for material treatment, e.g., for particle milling. In general, vibratory finishing processes utilize mixtures of particles of different masses, e.g., abrasives and parts to be finished. However, so far as I am aware, no successful coating system has been utilized to coat pellets, all having substantially the same mass, in a bed in which rolling circulation of the bed is induced by vibratory motion rather than by rotation.

More particularly, in the continuous pellet coating apparatus in accordance with the invention, an elongated trough has an inlet and an outlet separated from each other by a longitudinal distance along the direction of elongation of the trough. A feeder is provided for continuously delivering pellets to be coated into the trough at a location adjacent the inlet, and thereby establishes a bed of pellets in the trough which travel longitudinally along the trough as pellets are delivered by the feeder. A weir, disposed in the trough adjacent the outlet, has an edge over which pellets are discharged as pellets to be coated are delivered to the trough by the feeder. The weir establishes a maximum level of the bed of pellets in the trough. At least one spray nozzle is disposed above the maximum level of bed of pellets in the trough, and each spray nozzle is arranged to direct a spray of liquefied coating material toward pellets in the trough at an intermediate location between the inlet and outlet. A mechanical energy-imparting source, connected to the trough, vibrates the trough, and thereby maintains the bed of pellets therein in a substantially fluidized state, while rotating the bed so that substantially all of the pellets become exposed to the spray of liquefied coating material as they travel along the trough.

In one preferred embodiment of the coating apparatus, the elongation of the trough is linear, the trough is pivoted on an axis substantially parallel to its direction of elongation, and the mechanical energy-imparting source is connected to the trough at a location spaced laterally from the pivot axis, and arranged to apply impulse components to the trough as moments about the pivot axis. These impulse components have sufficient intensity to rotate the bed of pellets in the trough, so that substantially all of the pellets reach the surface of the bed and are exposed to the spray of liquefied coating material at times during their travel from the inlet to the outlet.

Because there is no need for a rotating cylinder, the coating apparatus can be scaled down to a relatively small size while allowing all or part of the spray nozzle assembly to be positioned at any distance above the pellets in pellet bed. Another advantage of the elimination of the rotating cylinder is that the bed of pellets does not need to travel along a straight path. The bed can travel in a circular, arcuate, or helical path, for example.

The mechanical energy-imparting source is preferably arranged to apply impulse components having sufficient intensity to rotate the bed of pellets in the trough, so that substantially all of the pellets reach the surface of the bed and are exposed to the spray of liquefied coating material at times during their travel from the inlet to the outlet. The apparatus also preferably includes means for adjusting impulse intensity, amplitude, direction, and/or frequency.

In an embodiment of the invention, at least one additional weir, and preferably a series of longitudinally spaced weirs, is provided in the trough between the inlet and outlet to achieve improved uniformity of the residence time of the pellets in the trough.

In accordance with another aspect of the invention, an array of air holes is formed in the trough, and an enclosure cooperates with the trough to provide an air plenum. The enclosure can be situated either above or below the trough, and a blower is connected to the air plenum for causing air to flow through the air holes and through the bed of pellets. Optionally, enclosures can be arranged to provide air plenums both above and below the trough. The air can flow through the bed while the spray of liquefied coating material is directed toward the pellets, and can also flow through the bed while coating material is not being sprayed. Preferably, the air flows though the bed of pellets in the trough, and, from within the bed of pellets, outward from the trough through the air holes. However, it is also possible for the air to travel in the opposite direction, that is, into the pellet bed through the air holes in the trough.

The air holes can be incorporated into one or more intermediate weirs, which can be made hollow. For example, the coating apparatus can include at least one additional, hollow, weir in the trough between the inlet and outlet. The additional weir can have walls facing the inlet of the trough and the outlet of the trough, and one or both of the walls can have an array of air holes. An enclosure cooperating with the trough forms an air plenum, and a blower connected to the air plenum can be used to cause air to flow through the air holes in the hollow weir, and through the bed of pellets. Preferably, the air flows through the bed of pellets and outward through the air holes in the hollow weir. However, as in the previously described embodiment, in which air holes are formed in the bottom of the trough, the air can be made to flow in the opposite direction. In the previously described embodiment, the circulation of pellets is influenced both by the vibration of the trough and by the flow of air. In the case of a hollow weir, however, the air flows through the air holes horizontally or nearly horizontally, and has less effect on the circulating movement of the pellets.

In a preferred embodiment of the coating apparatus, a monitor is provided for monitoring a condition of the operation of the coating apparatus, and a control, responsive to the monitor, adjusts one or more operating parameters of the apparatus. The operating parameters that can be adjusted include the rate at which the feeder delivers pellets to be coated to the trough, air temperature, air flow, vibration amplitude, vibration intensity, vibration frequency, vibration direction, liquefied coating material spray rate and spray pressure.

Whether the trough is linear or curved, for example circular, arcuate, or helical, the mechanical energy-imparting source is arranged to apply impulse components to the trough, which, in turn, apply a force to the bed of pellets exceeding the force of gravity. The impulse components are oriented and timed to cause the bed of pellets in the trough to rotate continuously, so that substantially all of the pellets reach the surface of the bed and are exposed to the spray of liquefied coating material at times during their travel from the inlet to the outlet.

Where air flow is utilized in combination with vibration, a monitor may also be included for monitoring a condition of the operation of the coating apparatus, and a control, responsive to the monitor, may be provided for adjusting one or more of the previously mentioned operating parameters.

Where air flow is utilized, and especially where the air flow has a substantial vertical component affecting the movement of pellets in the pellet bed, the impulse components should apply a force to the pellet bed exceeding the resultant of the forces applied to the bed by gravity and by air flowing through the bed. Here again, the impulse components should be oriented and timed to cause the bed of pellets in the trough to rotate continuously, so that substantially all of the pellets reach the surface of the bed and are exposed to the spray of liquefied coating material at times during their travel from the inlet to the outlet.

Another, but related, aspect of the invention is a method of continuously coating pellets. The method comprises four operations that are carried out continuously. Pellets are fed continuously into an elongated trough at a first location along the length of the trough, and a bed of pellets is maintained in the trough, the bed continuously moving longitudinally in the trough. A spray of liquefied pellet coating material is directed toward the bed of pellets in the trough at an intermediate location along the length of the trough. The trough is vibrated so that the bed is substantially fluidized and the bed of pellets is caused to rotate so that substantially all of the pellets are exposed to the spray at times during their travel along the trough. Coated pellets are discharged over a weir in the trough at a discharge location longitudinally spaced from the first location. The coated pellets are collected as they are discharged. The intermediate location, at which the spray of coating material is directed toward the bed of pellets, is between the first location and the discharge location.

Where the elongation of the trough is linear, vibration of the trough may be carried out by applying impulse components to the trough as moments about an axis parallel to the direction of elongation of the trough, the impulse components having sufficient intensity to rotate the bed of pellets in the trough.

The liquefied pellet coating material can be sprayed toward the bed of pellets in the trough by one or more spray nozzles located at a sufficient distance from the pellets that the coating material reaches the pellets in a partially dried condition such that solvent in the coating material does not damage the surfaces of the pellets.

To make the pellet residence time in the trough more uniform, the bed of pellets can be moved along the trough over an additional weir at an intermediate location, or a series of longitudinally spaced weirs.

To minimize waste of coating material, or to aid in distribution of the coating material, air is also preferably caused to flow through the bed of pellets. The air can be caused to flow through the bed of pellets either inwardly or outwardly through an array of openings in the trough. The openings can be formed in one or more hollow weirs at intermediate locations along the length of the trough, and in that case, the flow of air through the openings can be horizontal or nearly horizontal. Here again the flow of air can be either into the trough, or outward from the trough, through the array of openings in the hollow weir.

A condition of the coating process is preferably monitored, and one or more of the previously mentioned operating parameters can be adjusted automatically in response to the monitored condition.

In batch coating of tablets, the tablet bed can be relatively deep. However, in this invention, coating is a continuous process rather than as a batch process. In a continuous coating process it is desirable to maintain a relatively shallow tablet bed. In a preferred embodiment of the invention, excessive bed depth can be avoided by mounting the trough so that it tilts downward. That is, the trough is mounted so that its exit end is lower than its inlet end. By adopting an appropriate degree of downward tilt, depth of the tablet bed in the trough can be maintained substantially constant along the length of the trough.

In a preferred embodiment of the invention, it is also desirable to finish the inner surface of the trough so that it has a small amount of roughness. A very smooth "mirror" finish, having an average surface roughness Ra of less than about 0.05 μm, is typical in a rotating drum coater. However, in the case of a vibrating trough, depending on the frictional coefficients of the tablets, a similar finish may not exhibit sufficient friction to achieve reliable tablet bed rotation. For the coating apparatus of the invention, good results have been achieved for a variety of tablets, using a trough having an average surface roughness, Ra, in the range from approximately 0.2 μm to 0.8 μm.

One or more operating parameters can be adjusted automatically in response to a monitored process condition when air is caused to flow through the bed of pellets.

The invention has many advantages over conventional coating apparatuses and methods, especially in its capability of being scaled down, its controllability, and its ability to reduce damage to the product being coated. When the coating apparatus is scaled down, the reduced bed depth can also reduce weight-induced damage to the product. Moreover, with the invention, a batch process coating stage can be replaced by a continuous coating stage at various throughput volumes, and the continuous coating stage can be linked with other upstream and downstream continuous processing stages.

Other details and advantages of the invention will be apparent from the following detailed description when read in conjunction with the drawings.

DETAILED DESCRIPTION OF THE PREFERRED EMBODIMENT

The term "pellets," as used herein, includes solid, or at least externally solid, orally delivered pharmaceutical dosage forms, vitamins, candies, chewing gum, breath mints, animal feed, and the like. Usually, all of the pellets being coated by the method and apparatus described herein will be of substantially the same size and composition.

Figure 1:
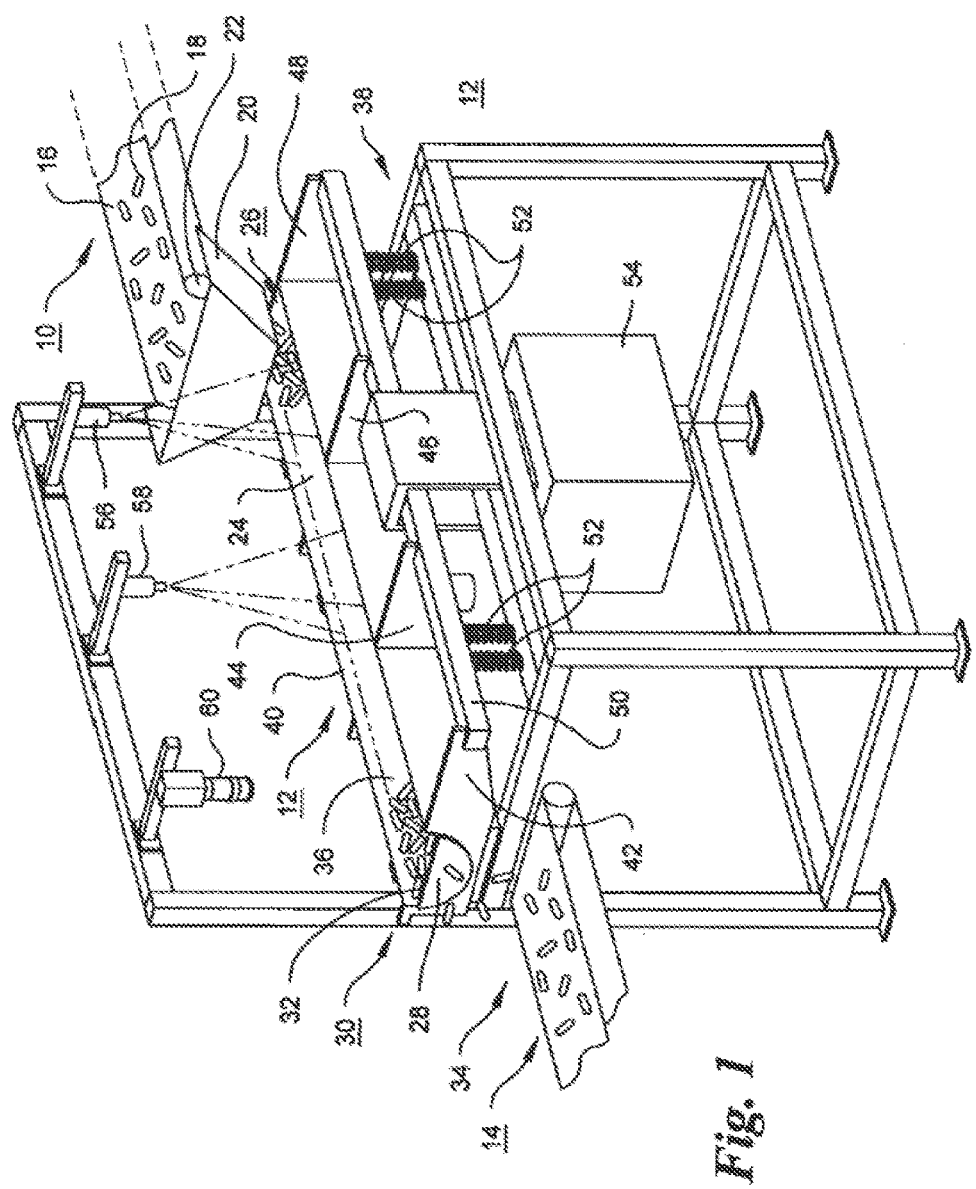
FIG. 1 is a schematic perspective view of a continuous coating apparatus in accordance with a preferred embodiment of the invention.

The coating apparatus of FIG. 1 comprises three main sections: a feeder section 10, a coating section 12, and a discharge section 14.

The feeder section 10 can be any of a variety of mechanisms suitable for delivering pellets to be coated to a desired location continuously at a defined average rate. In FIG. 1, the feeder comprises a conveyor belt 16, on which pellets 18 are carried to a chute 20. The rate at which the feeder delivers pellets through the chute should be adjustable, and in the case of a belt conveyor, the feed rate can be adjusted by controlling the speed of a drive motor (not shown in FIG. 1) connected to a belt-driving drum, e.g., drum 22. The rate at which the feeder delivers pellets does not need to be well-defined over a short interval such as a few seconds. However, the rate should be capable of being reasonably well-defined over a longer interval such as a minute, e.g., an average rate of 1000±100 pellets per minute. Various alternative forms of feeding mechanisms such as vacuum conveyors, screw conveyors, elevators, vibrating conveyors and other suitable conveyors can also be used.

Pellets drop through the chute 20 into an elongated, vibrating, trough 24, at a location preferably adjacent one end of the trough, which will be referred to as a trough "inlet." In FIG. 1, the inlet is designated by reference numeral 26. The trough may be open as in FIG. 1, or may be enclosed so that an air plenum is formed as will be described later. In the latter case, the inlet is a location adjacent a opening in the enclosure, which may be either controlled or uncontrolled. A weir 28, is disposed at an outlet location or "outlet" 30, spaced longitudinally from the inlet 26, and preferably located at the end of the trough opposite from the inlet 26. The weir has an upper edge 32, over which pellets are discharged from the trough onto a collector 34, which can be in the form of a belt conveyor or hopper. The weir shown in FIG. 1 is in the form of a segment-shaped plate. Alternatively, a ramp can be used, at the outlet of the trough, and the term "weir," as used herein, includes ramps and other similar barriers over which pellets can be discharged.

The upper edge of the weir 28 can be horizontal, or slanted, and need not be straight. However, regardless of the shape of its upper edge, the weir establishes a maximum level for the bed 34 of pellets in the trough. As will be described, the pellets in the bed are substantially fluidized, that is, made readily flowable, by the vibration of the trough. Thus, as pellets are fed at a given rate to the inlet of the trough, the bed slowly moves toward the outlet, and pellets are discharged from the outlet at substantially the same rate. As vibration takes place, the upper surface of the fluidized bed of pellets will ordinarily be disposed at an angle in the range of about 10 to 20 degrees from the horizontal, depending on various factors such as the magnitude of the vibrations, air flow though the bed, the properties of the pellets, etc. However, in some cases, the surface of the bed can reach an angle of 45 degrees or more.

The trough 24 is flexibly supported on a frame 38 by a set of resilient supports (not shown in FIG. 1) along one of its sides 40. These supports effectively establish a pivot axis extending alongside the trough and substantially parallel to the direction of elongation of the trough. The pivot axis, although preferably alongside the trough, can be inside the trough, or above or below the trough.

The trough is connected by a set of arms 42, 44, 46 and 48, to a bar 50, which extends longitudinally along the trough on the side opposite to the side on which the trough is pivoted. The bar 50 is mounted on the frame by springs 52, and connected to an energy-imparting source 54, which applies rapidly repeated mechanical impulses to the bar. In the apparatus shown, the impulses are applied vertically upward to the bar. However the impulses can be applied in any direction other than directly toward the pivot axis of the trough, so that the impulses are applied as moments about the pivot axis.

The repeated impulses must have sufficient intensity to fluidize the bed of pellets in the trough, and at the same time cause rotation of the bed of pellets so that pellets circulate continuously from the lower portions of the bed to the surface, and then back to the lower portions of the bed. The impulses must therefore be sufficient to overcome the effect of gravity on the pellet bed, taking into account also the effect of any air flowing upward or downward through the bed. The movement of the bar 50 will ordinarily be in the range of 0.1 to 5 mm. The intensity of the impulses, of course, depends not only on their amplitude, i.e., the range of movement of the bar 50, but also on the rate of movement of the bar, i.e., the slopes of the leading and trailing edges of each impulse when the amplitude of movement of the bar is plotted against time. The rotation and fluidization of the pellet bed are influenced not only by the intensity of the impulses, but also by the frequency at which the impulses are applied, the frequency being preferably in the range from about 500 to 3500 Hz.

The energy-imparting source 54 can be any of a variety of mechanisms for producing mechanical vibrations, such as electric motors having eccentric weights mounted on their shafts, linear devices such as electromagnetic vibrators, servomotors, etc. The energy imparting source can be composed of plural energy-imparting units, if appropriately synchronized. Servomotors are preferable because they are easily controlled.

Preferably, one or more parameters of the impulse components, such as intensity, amplitude, direction, or frequency is adjustable, and suitable adjusting means can be included as part of the energy-imparting source. The adjusting means can be, for example, an electrical motor speed control, a source of electrical pulses for operating an electromagnetic vibrator, or any of a wide variety of equivalent adjusting devices. In the case of adjustment of direction, the adjusting means can be, for example, a mechanism for moving the energy-imparting source itself or its output shaft or arm, or a mechanism for adjusting the relative amplitudes of impulses delivered by two or more sources coupled together in order to adjust the direction of a resultant impulse. The adjusting means can be adjusted manually, or automatically, with or without feedback from one or more sensors used to monitor conditions of the coating operation such as coating thickness, pellet feed rate, and the like.

On the inside of the trough, a smooth mirror finish, that is, a finish having an average surface roughness Ra of less than about 0.05 µm, should be avoided because, for some tablets, it will not exhibit sufficient friction to achieve reliable tablet bed rotation. For the coating apparatus of the invention, good results can be achieved for a broad variety of tablets, using a trough having an average surface roughness, Ra, in the range from approximately 0.2 µm to 0.8 µm.

Spray nozzles 56 and 58 are mounted on the frame and arranged to direct fan-shaped spray patterns of liquefied coating material downward toward the bed of pellets in the trough at intermediate locations between the inlet 26 and the outlet 30. The fan-shaped spray patterns are preferably relatively wide in the direction of the trough and relatively narrow in the direction of the width of the trough.

The coating material can be any of a variety of known coating materials. In the case of pharmaceutical tablets, for example, the coating material can be a combination of a polymer such as polyvinylpyrollidone (PVP) or hydroxypropylcellulose (HPC), together with a pigment and an opacifier such as titanium dioxide ($TiO_2$), in a suitable vehicle such as water or an organic solvent, which partially evaporates as the spray approaches the bed of pellets.

Various devices can be used to monitor the condition of the coating applied to the pellets. In FIG. 1, a sensor 60 is mounted on the frame 38 above the pellet bed at a location downstream of the second spray nozzle 58 with respect to the direction of travel of the pellet bed in the trough. The sensor is associated with a monitor (not shown in FIG. 1), which can be a spectrometer for monitoring the thickness of the coating on the pellets. A feedback signal from the spectrometer can be used to control the rate at which uncoated pellets are fed to the trough by the feeder section 10. Other conditions in the coating apparatus such as temperature and humidity can be monitored, and the coating thickness as well as these other conditions can be used, individually or in combination, to control operating parameters such as pellet feed rate, vibration amplitude, vibration intensity (which depends on both amplitude and the rate of change of amplitude), vibration frequency, coating spray velocity and spray pressure. Where air is caused to flow through the bed of pellets, the temperature and flow rate of the air can also be controlled in response to one or more monitored conditions.

Figure 2:
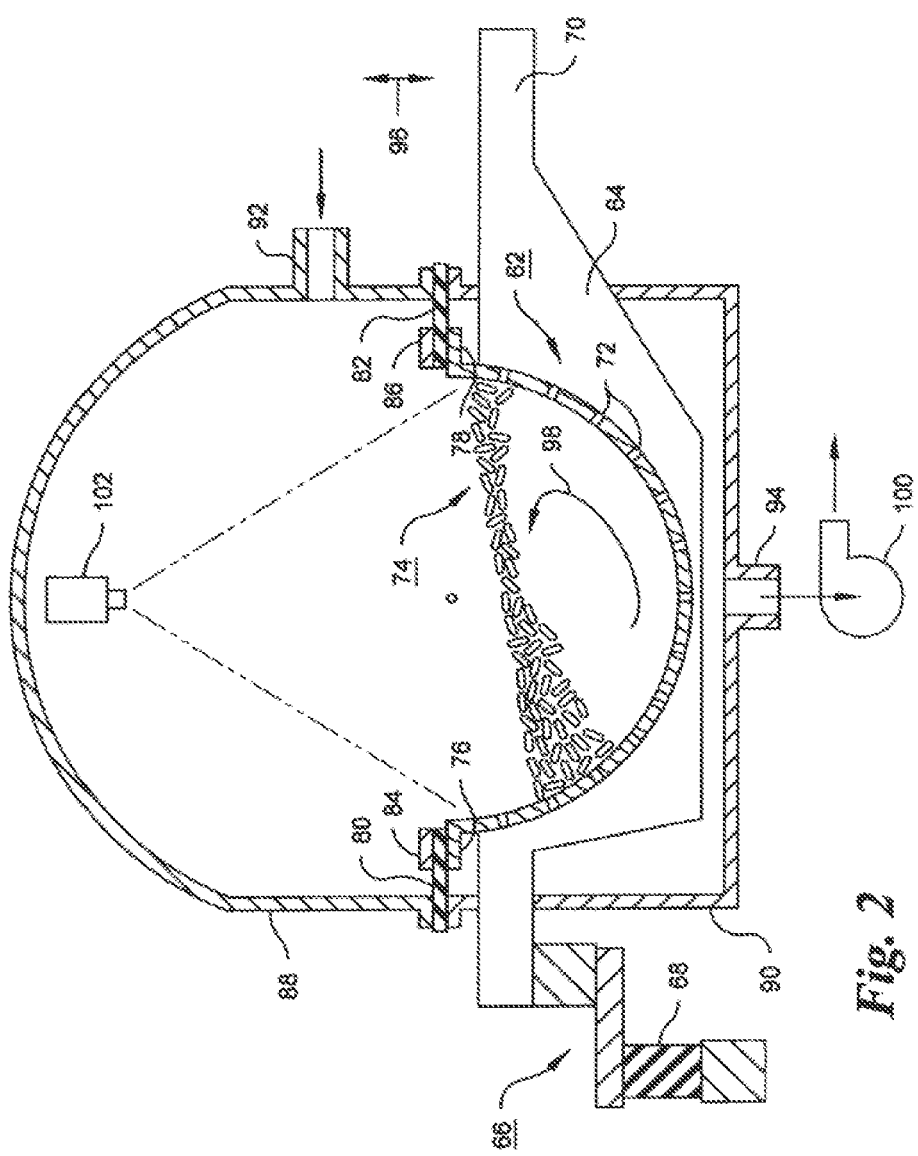
FIG. 2 is a transverse cross-sectional view of the trough in the continuous coating apparatus having air plenums.

FIG. 2 shows a version of the coating apparatus according to the invention in which an array of air passages is formed in the trough, and upper and lower air plenums are formed by cooperation of the trough with enclosures respectively above and below the trough. These air plenums are provided in order to maintain a flow of air through the air passages and through the bed of pellets in the trough.

The trough 62 is a vibrating trough, supported on a set of arms similar to arms 42-48 in FIG. 1. One such arm, 64, is shown in FIG. 2, and is supported at one end on a mounting structure 66, which includes an elastomeric bar 68. The opposite end 70 of the arm 64 is connected to a energy source (not shown) similar to energy source 54 in FIG. 1.

An array of air passages 72 is formed in the trough. The passages are smaller than the pellets in the pellet bed 74 in the trough, and situated so that most of the openings are below the top of the bed.

The trough is provided with a pair of flanges 76 and 78, which extend longitudinally along its upper edges. Elastomeric sealing strips 80 and 82 are clamped between the respective flanges and clamping strips 84 and 86, and extend between flanges of upper and lower enclosures 88 and 90.

An upper enclosure 88 has an air passage 92, and the lower enclosure 90 has an air passage 94. The pellet bed 74 is fluidized as a result of vibrations imparted to the trough through the arms including arm 64, which vibrates up and down about an axis at the location of elastomeric bar 68 in the directions indicated by the double-ended arrow 96. The motion of the trough substantially fluidizes the bed of pellets, and causes the pellets to circulate in a rotating path as indicated by arrow 98. In the embodiment shown in FIG. 2, air passes into the upper plenum through passage 92, downward through the pellet bed 74 and passages 72 into the lower plenum, and outward through passage 94 and blower 100. The upper and lower enclosures do not need to be sealed perfectly, and in the embodiment shown, for example, the arms on which the trough are mounted extend through slots in the lower enclosure 90. Pellets are fed into, and discharged from, the vibrating trough, through suitable airlocks (not shown), for example, through rotary plate feeders of the kind illustrated in U.S. Pat. No. 6,416,261, dated Jul. 9, 2002, the disclosure of which is incorporated by reference.

The flow of air through the bed of pellets provides for more uniform distribution and drying of the coating material, and reduces the loss of particles of the spray from the spray nozzles, e.g., nozzle 102, to the atmosphere. Although in the embodiment shown, the flow of air through the pellet bed is maintained by drawing air outward from the lower plenum by a blower 100, as an alternative, air can be forced into the upper plenum through passage 92. In some instances it may be desirable to maintain an upward flow of air, i.e., a flow of air into the pellet bed in the trough through the holes 72. In that case, blower 100 can be arranged to blow air into the lower plenum through passage 94, or a blower can be used to draw air outward from the upper plenum through passage 92. In any of these embodiments, the temperature and humidity of the air flowing through the bed of pellets can be controlled in order to maintain proper coating conditions.

Although it is preferred to have both an upper air plenum and a lower air plenum, advantages of air flow through the pellet bed can also be realized in a coating apparatus having only an upper air plenum, or only a lower air plenum. Moreover, although it is desirable, but not absolutely essential, to provide airlocks for feeding pellets to, and discharging pellets from, the trough in the case in which an upper air plenum is used, airlocks are entirely unnecessary in the case of a coating apparatus having only a lower plenum.

Figure 3:
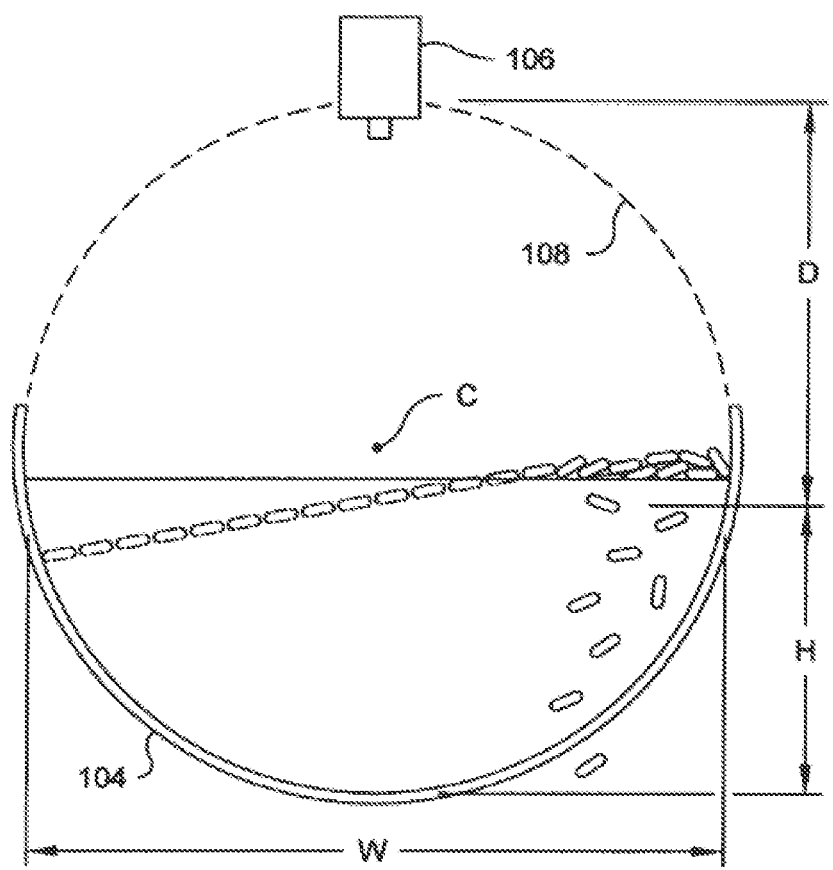
FIG. 3 is a schematic diagram illustrating the relationship of a spray nozzle to the bed of pellets in the trough of a continuous coating apparatus corresponding to the apparatus of FIG. 1.

As shown schematically in FIG. 3, a typical trough 104 has an arcuate cross-section. In this case, the arc is centered on a center line C (shown endwise as a point in FIG. 4). Pellets are discharged from the pellet bed in the trough over the upper edge of a weir.

As the trough is vibrated, the weir maintains the top of the fluidized pellet bed substantially at a fixed position so that the center of the top of the pellet bed remains at a constant height H, measured from the bottom of the trough. As mentioned previously, while vibration takes place, the top of the bed will ordinarily be at an angle in the range of about 10 to 20 degrees from horizontal. However, depending on the intensity and direction and frequency of the vibrations of the trough, the pattern of circulation of the pellets in the trough, and other factors such as air flow and the nature of the pellets, the top of the bed can be disposed at an angle outside the 10 to 20 degree range.

As shown in FIG. 3, the bed, if at rest, would have a width W, measured in a direction transverse to the direction of elongation of the trough. Because the pellet bed is coated in a vibrating trough, instead of in a conventional rotating drum, it is possible for the spray nozzle 106, or parts of the spray nozzle, to be located above the cylinder 108 that would be formed if the arcuate inner wall of the trough were continued to form a complete cylinder. Thus, even in a coating apparatus having a pellet bed with a relatively small cross-sectional area, it is possible to position the spray nozzles far enough from the top of the bed that the sprayed coating material will dry sufficiently before it reaches the pellet bed, so that the solvents in the coating material do not damage the surfaces of the pellets and impair coating quality.

In the case of an arcuate trough, the vertical distance D from the center of the top surface of the bed and the arc extension 108 is given by the formula $D=W^2/4H$. Thus, parts of the nozzle assembly can be at a distance greater than D from the center of the top of the pellet bed, that is, beyond the arcuate extension of the inner wall of the trough.

Figure 4:
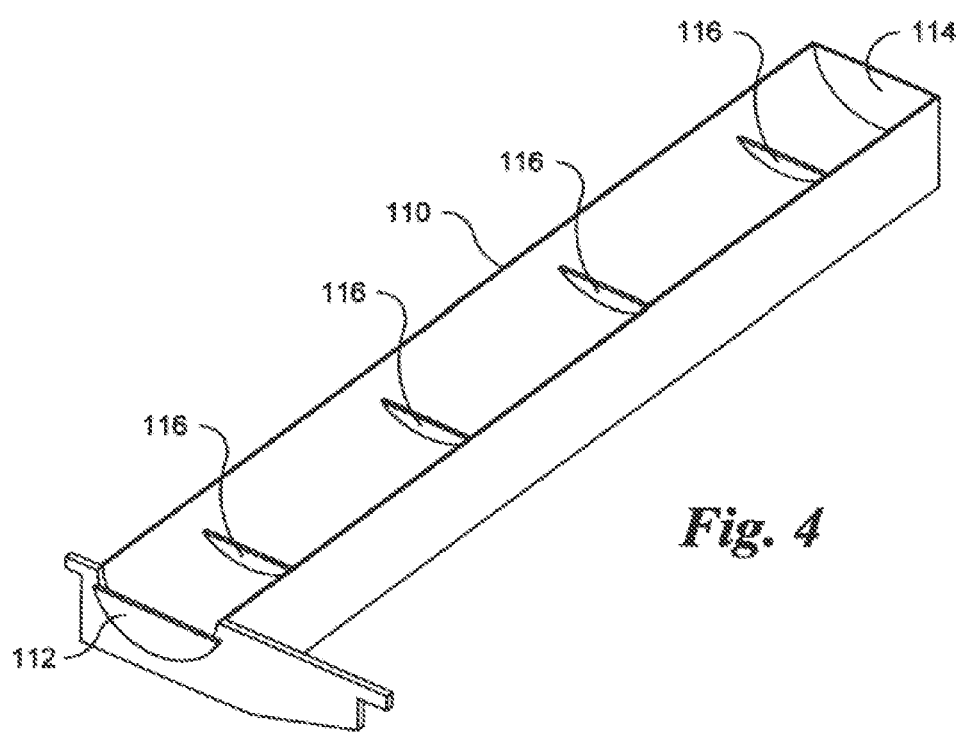
FIG. 4 is a schematic perspective view of a vibratory trough having intermediate weirs.

The trough 110 shown in FIG. 4 can be used in the coating apparatus of FIG. 1, or in the coating apparatus of FIG. 2. This trough 110 has a discharge weir 112 at one end, a barrier 114 at the opposite end, which is higher than the discharge weir, at the opposite end, and a series of intermediate weirs 116. The height of each of the intermediate weirs is preferably less than the height of the discharge weir 112, and is also preferably such that each of the intermediate weirs is entirely underneath the surface of the pellet bed when the trough is vibrating. The intermediate weirs block longitudinal movement of lower parts of the pellet bed and improve the uniformity of the residence time of each pellet in the trough. It is possible to use a single intermediate weir or a plurality of intermediate weirs as shown.

Figure 5:
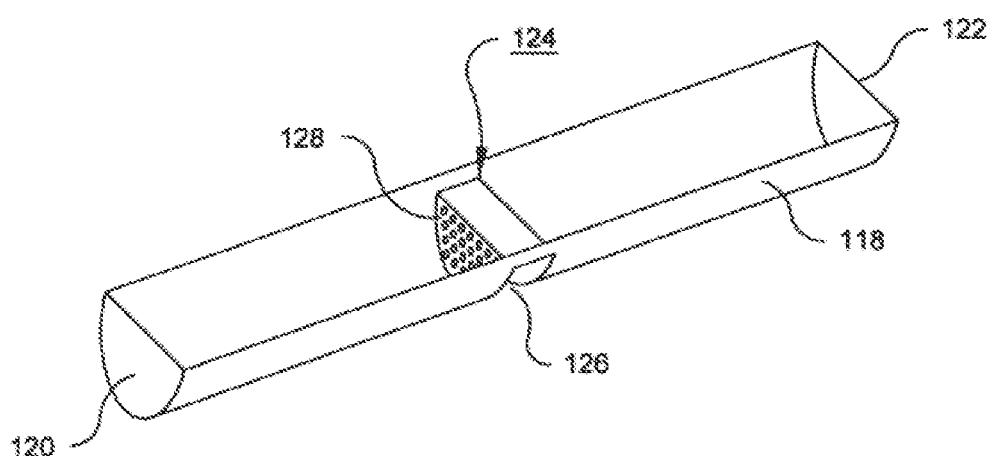
FIG. 5 is a schematic perspective view, corresponding to FIG. 2, illustrating an alternative embodiment of the trough, having a hollow, perforated, intermediate weir.

One or more intermediate weirs can also be made hollow and provide with an array of holes for passage of air into or out of a trough. For example, as shown in FIG. 5, a trough 118, having a discharge weir 120 at one end and a barrier 122 at the opposite end, is formed with an intermediate weir 124. The intermediate weir is hollow, forming a tunnel 126 extending underneath the trough in a direction transverse to its longitudinal direction. The wall 128 of the weir, which faces toward the discharge end of the trough, is preferably, but not necessarily, vertical or nearly vertical, and has an array of air passages. The opposite face of the intermediate weir (not shown in FIG. 5) can have a similar array of air passages. The trough of FIG. 5 can be used in a coating apparatus having an upper air plenum, a lower air plenum, or both as in FIG. 2. Because the air passages are in walls of the weir that are either vertical or nearly vertical, the vertical component of the velocity of the air flow through the pellet bed is small and has only a negligible effect on the circulation of pellets resulting from vibration of the trough. However, the air flow can be effective in maintaining uniform coating conditions. Here, as in the embodiment of FIG. 2, the air flow can be directed either inward through the air passages to the pellet bed, or outward from the pellet bed through the air passages. The hollow weir also has the advantage of achieving a more uniform residence time, and, of course, plural hollow weirs can be provided in a trough.

Figure 6:
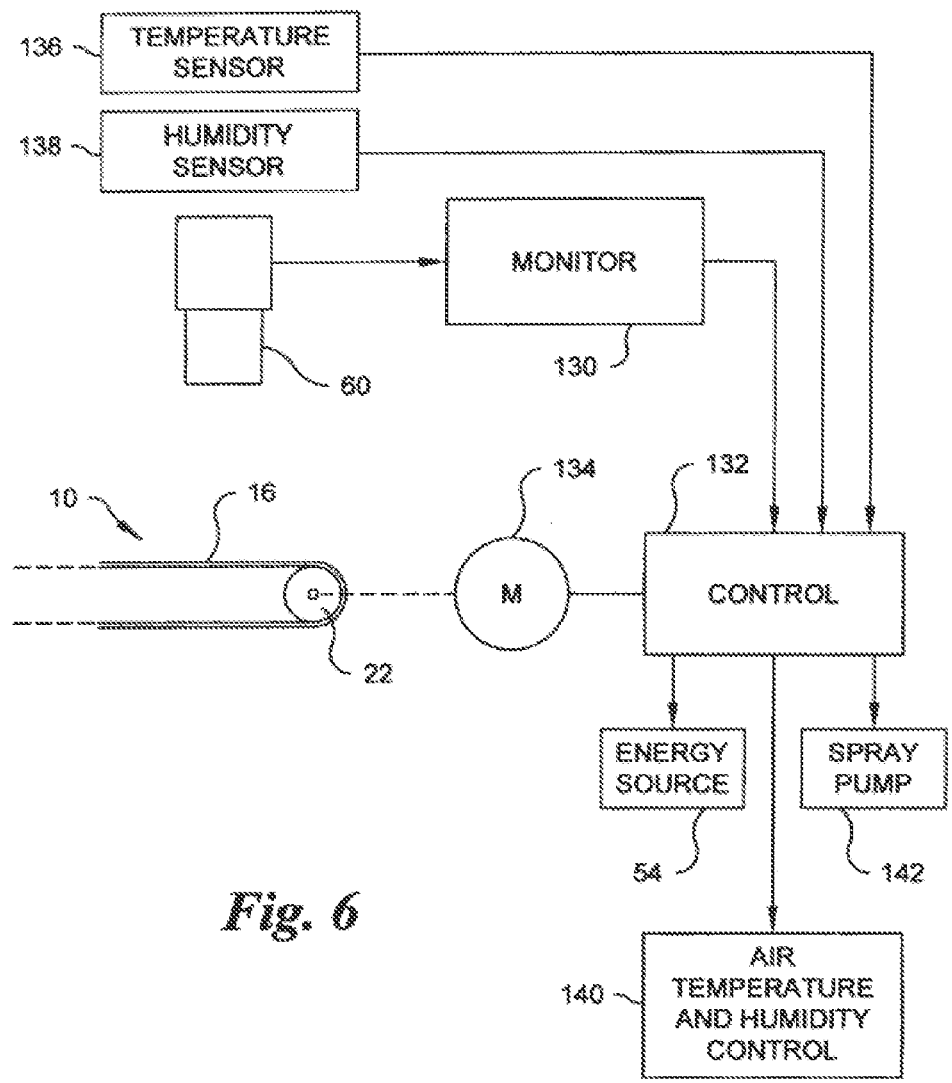
FIG. 6 is a schematic diagram of monitoring and control components for the continuous coating apparatus.

In the control system depicted in FIG. 6, the spectrometer 60 (FIG. 1) is sensitive to the color of the coating on the pellets in the pellet bed passing underneath it. The color is a function of coating thickness. A monitor 130, e.g., a spectrometer, responsive to the sensor 60, generates a signal corresponding to coating thickness, and operates a motor control 132, which, in turn, controls the speed of a servomotor 134 which operates the pellet feeder 10. If the coating becomes too thin, the rate at which pellets are fed to the trough can be reduced, and their residence time in the trough will be increased. Thus, a uniform coating thickness can be maintained.

Other monitoring features and controls can be utilized. For example, the signal from the monitor 130 can be used to control the vibration rate or intensity, or spray velocity, in addition to, or as an alternative to, controlling the pellet feed rate. The temperature and/or humidity of the exhaust air can also be monitored and used to control operating parameters or combinations thereof, including air temperature, humidity, spray velocity, as well as pellet feed rate, and trough vibration rate or intensity. As shown in FIG. 6, the control 132 can also receive inputs from an air temperature sensor 136 and a humidity sensor 138, and delivers control signals to an air temperature and humidity control 140 and a spray pump 142.

Figure 7:
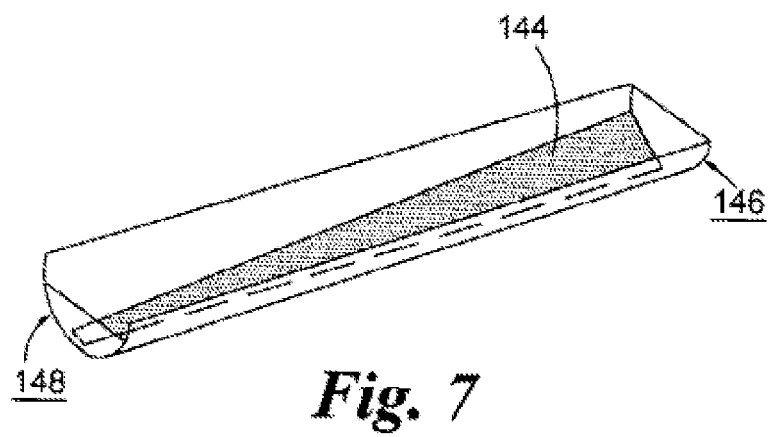
FIG. 7 is a schematic diagram of a horizontal vibratory trough, showing the relationship between the trough and the tablet bed.
Figure 8:
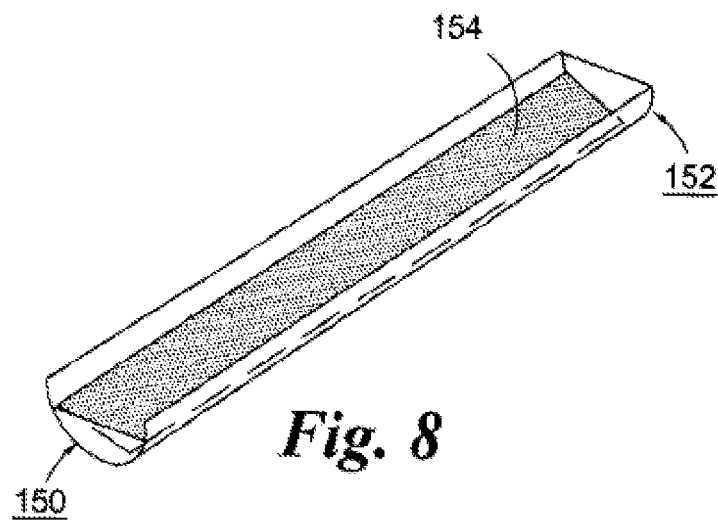
FIG. 8 is a schematic diagram of a downwardly tilted vibratory trough, showing the relationship between the trough and the tablet bed.

Although satisfactory results can be achieved with the trough of the coating apparatus disposed horizontally, by tilting the trough downward in the direction of travel of the pellets along the trough, so that the outlet end of the trough is lower than the inlet end, the depth of the tablet bed can be made more nearly uniform along the length of the trough thereby reducing the maximum depth of the bed. As shown in FIG. 7, in the case of a horizontal trough, the depth of the tablet bed 144 gradually decreases from the inlet end 146 of the trough toward the outlet end 148. The shape of the tablet bed in the trough is affected by the tablet feed rate, by the vibration of the trough, by drag due to friction between the tables and the inner surface of the trough, and by gravity. Thus, the surface of the tablet bed slopes downward from the side at which the magnitude of trough vibration is maximum toward the opposite side of the trough, and also from the inlet end toward the outlet end. In the case of a downwardly tilted trough, as shown in FIG. 8, where the outlet end 150 is lower than the inlet end 152, surface of the tablet bed 154 slopes downward from the side at which the magnitude of trough vibration is greater toward the opposite side. However, the slope of the tablet bed surface in the direction along the length of the trough is approximately the same as the angle of downward tilt of the trough. Thus, the cross-section of the tablet bed is maintained nearly constant along the length of the trough, the tablet bed is not excessively deep adjacent the inlet end of the trough, and more uniform coating of the tablets can be achieved. The uniformity of the depth of the tablet bed, of course depends on the tablet feed rate at the inlet end of the trough. Therefore, the degree of tilt of the trough should be matched to the tablet feed rate. Thus, the pellets should be fed at a rate that maintains the surface of the bed of pellets substantially parallel to the direction of elongation of the trough.

Various other modifications can be made to the apparatus and method described above. For example, although the trough can be open as shown in FIG. 1, or provided with an upper air plenum as shown in FIG. 2, as an alternative, the trough can be the lower part of a closed channel that is vibrated. The closed channel can even have a circular cross-section if sufficiently large that the spray nozzles are not too close to the pellet bed. However, in most cases, and especially where the apparatus is built on a scale suitable for continuous coating of relatively small quantities of pellets such as prescription drugs, if the trough is a lower part of a closed channel, the channel will have a non-circular shape, with a vertically elongated transverse cross-section.

Whereas the continuous coating apparatus described above comprises a linear trough, various alternative configurations are possible. For example, the trough can have a toroidal configuration similar to that of the vibration mill described in U.S. Pat. No. 3,100,088, granted on Aug. 6, 1963 to H. L. Podmore et al. and incorporated herein by reference. In that case, as described by Podmore et al. the impulses imparted to the toroidal container by an eccentric weight on a centrally located motor will cause circulating movement of pellets in the container as they travel along the length of the trough. Another example is a configuration in which the coating apparatus is composed of a series of vibrating troughs, located one above another, and arranged so that pellets are fed from an upper trough to a next trough, and the pellet beds travel in alternating directions in the respective troughs. Still other trough configurations, such as an arcuate configuration, or a helical configuration as in U.S. Pat. No. 5,067,431, granted on Nov. 26, 1991 to Charles E. Heitmiller, can also be utilized.

The above modifications, and numerous other modifications, can be made to the invention described without departing from its scope, as defined by the following claims.

The invention claimed is:

1. A process for continuously coating pellets comprising:
feeding pellets continuously into a linearly elongated trough, said trough having a concave trough bottom wall extending laterally from a first longitudinal side edge to an opposite second longitudinal side edge, said pellets being introduced into the trough at a first location along the length of the trough, and thereby maintaining a bed of pellets continuously moving longitudinally in the trough;
directing a spray of liquefied pellet coating material toward the bed of pellets in the trough at least at one intermediate location along the length of the trough;
causing reciprocating rotational vibration of the trough about a pivot axis parallel to the direction of elongation of the trough but laterally offset from a longitudinal centerline of the trough, said centerline being positioned above a location on said concave trough bottom midway between said first and second longitudinal side edges by applying impulse components to the trough as moments about said pivot axis, said reciprocating rotational vibration having sufficient intensity substantially to fluidize the bed of pellets disposed in said trough, thereby causing the pellets in said bed to circulate, substantially continuously and in the same direction, in a loop-shaped path transverse to the direction of elongation of the trough, as they move longitudinally in the trough, so that substantially all of the pellets are exposed to the spray at times during their travel along the trough; and
collecting coated pellets discharged over a weir in the trough at a discharge location longitudinally spaced from the first location, the at least one intermediate location at which the spray is directed toward the bed of pellets being between the first location and the discharge location.

2. The process of claim 1, in which said pivot axis is a stationary pivot axis.

3. The process of claim 1, in which the liquefied pellet coating material is sprayed toward the bed of pellets in the trough by a spray nozzle located at a sufficient distance from the pellets that the coating material reaches the pellets in a partially dried condition such that solvent in the coating material does not damage the pellets.

4. The process of claim 1, in which the bed of pellets is moved along the trough over at least one additional weir in the trough, the additional weir being spaced longitudinally from the weir at the discharge location.

5. The process of claim 1, in which the bed of pellets is moved along the trough over a series of longitudinally spaced weirs in the trough in addition to the weir at the discharge location.

6. The process of claim 1, in which air is caused to flow through the bed of pellets while the spray of liquefied pellet coating material is directed toward the bed of pellets.

7. The process of claim 1, in which the bed of pellets is moved along the trough over at least one hollow weir in the trough, spaced longitudinally from the weir at the discharge location, and in which air is caused to flow through the bed of pellets and outwardly from the trough through an array of openings in the hollow weir while the spray of liquefied coating material is directed toward the bed of pellets.

8. The process of claim 1, in which a condition of the coating process is monitored, and, in response to the monitored condition, at least one operating parameter is adjusted automatically in response to the monitored condition, the operating parameter being from the group consisting of the rate at which the pellets to be coated are fed to the trough, air temperature, air flow, vibration amplitude, vibration intensity, vibration frequency, vibration direction, liquefied coating material spray rate and spray pressure.

9. The process of claim 8, in which air is caused to flow through the bed of pellets while the spray of liquefied pellet coating material is directed toward the bed of pellets.

10. The process of claim 1, in which the outlet end of the elongated trough is lower than the inlet end, whereby the trough is tilted downward in the direction of travel of pellets in the trough, and in which, in the feeding of pellets continuously into the trough at said first location, pellets are fed at a rate that maintains the surface of the bed of pellets substantially parallel to the direction of elongation of the trough.

11. The process of claim 1, in which the vibration of the trough is carried out at a frequency in the range from 500 to 3500 Hz.

12. The process of claim 1, in which said pivot axis extends alongside the trough.

13. The process of claim 1, in which said pivot axis extends alongside the trough on one side of the trough, and said impulse components are applied to the trough through an arm structure extending from the opposite side of trough and away from the trough.

* * * * *